United States Patent
Ikemoto et al.

(10) Patent No.: US 7,521,545 B2
(45) Date of Patent: Apr. 21, 2009

(54) AZO COMPOUNDS AND PROCESS FOR PRODUCTION THEREOF

(75) Inventors: Tomomi Ikemoto, Osaka (JP); Takeshi Yamasaki, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 11/661,183

(22) PCT Filed: Aug. 25, 2005

(86) PCT No.: PCT/JP2005/015390

§ 371 (c)(1),
(2), (4) Date: Feb. 26, 2007

(87) PCT Pub. No.: WO2006/022311

PCT Pub. Date: Mar. 2, 2006

(65) Prior Publication Data

US 2008/0009539 A1 Jan. 10, 2008

(30) Foreign Application Priority Data

Aug. 27, 2004 (JP) ............................. 2004-248217

(51) Int. Cl.
*C07D 307/79* (2006.01)
*C07D 405/04* (2006.01)
(52) U.S. Cl. .................. 534/581; 534/787; 548/454
(58) Field of Classification Search ............... None
See application file for complete search history.

(56) References Cited

U.S. PATENT DOCUMENTS

| 6,172,085 B1 | 1/2001 | Ohkawa et al. |
| 6,878,831 B2 | 4/2005 | Aoki et al. |
| 7,034,166 B2 | 4/2006 | Tawada et al. |
| 2004/0034049 A1* | 2/2004 | Okawa et al. ............... 514/278 |
| 2005/0171184 A1 | 8/2005 | Aoki et al. |
| 2006/0142598 A1 | 6/2006 | Tawada et al. |

FOREIGN PATENT DOCUMENTS

| JP | 10-330380 | 12/1998 |
| JP | 2002-265460 | 9/2002 |
| JP | 2003-104981 | 4/2003 |

OTHER PUBLICATIONS

Fukatsu, Kohji et al., "Synthesis of TAK-218 using (R)-2-methylglycidyl tosylate as a chiral building block", Tetrahedron: Asymmetry vol. 10, 1999, pp. 1521-1526.

* cited by examiner

*Primary Examiner*—Fiona T Powers
(74) *Attorney, Agent, or Firm*—Foley & Lardner LLP

(57) ABSTRACT

A process for the production of an aromatic azo compound having a 2,3-dihydrobenzofuran ring bearing a diazo group at the 5-position of the ring by conducting the diazo coupling of a 2,3-dihydrobenzofuran derivative represented by the general formula (II):

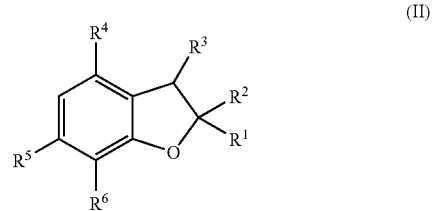

[wherein $R^1$ and $R^2$ are each independently $C_{1-6}$ alkyl; $R^3$ is optionally substituted aryl; and $R^4$, $R^5$ and $R^6$ are each independently hydrogen, $C_{1-6}$ alkyl, halogeno, $C_{1-6}$ alkoxy, or $C_{1-6}$ alkylthio] with a benzenediazonium salt having an electron-withdrawing group at the p- and/or o-position in a mixed solvent composed of water and a polar organic solvent.

7 Claims, No Drawings

AZO COMPOUNDS AND PROCESS FOR PRODUCTION THEREOF

TECHNICAL FIELD

The present invention relates to an aromatic azo compound having a 2,3-dihydrobenzofuran ring bearing a diazo group at the 5-position of the ring, and a process for producing a 2,3-dihydrobenzofuran derivative bearing an amino or fused cyclic amino group at the 5-position of the ring by using the azo compound as a starting material.

BACKGROUND ART

Many of compounds having a 2,3-dihydrobenzofuran ring bearing a substituted amino group at the 5-position of the ring have useful physiological activities and are important starting materials for medical products. Therefore, there are wide demands for industrially advantageous processes for producing 2,3-dihydrobenzofuran derivatives having an amino group at the 5-position of the ring as precursors thereof.

Heretofore, for introducing a substituted amino group at the 5-position of a 2,3-dihydrobenzofuran ring in known synthesis methods, a 2,3-dihydrobenzofuran is constructed by using a phenol derivative wherein the substituted amino group has been introduced at the desired position as a starting material, or a 2,3-dihydrobenzofuran which is unsubstituted at the 5-position of the ring is subjected to nitration or nitrosation and then to a reducing reaction to introduce an amino group as described in Patent Document 1. Further, Patent Document 2 discloses a method for introducing an amino group into a 2,3-dihydrobenzofuran ring at the 5-position of the ring by brominating the 5-position of the 2,3-dihydrobenzofuran, reacting the resulting product with benzylamine to replace a bromo group with a benzylamino group, and subjecting to catalytic reduction for debenzylation of the benzylamino group.

On the other hand, if a diazo group could be introduced into a 5-position of a 2,3-dihydrobenzofuran ring by diazo coupling of a 2,3-dihydrobenzofuran derivative with a benzenediazonium salt, an amino group would be easily introduced into the 5-position of the 2,3-dihydrobenzofuran derivative by reducing the diazo compound obtained by the diazo coupling. However, the diazo coupling between a 2,3-dihydrobenzofuran derivative and a benzenediazonium salt does not proceed at all under conventional diazo coupling conditions. Generally, as a solvent for diazo coupling, water is used and, in some cases, a mixed solvent of water and an organic solvent is used. For example, Patent Document 3 and non-Patent Document 1 disclose the use of a mixed solvent of water and acetic acid as a solvent for diazo coupling of a 2,3-dihydrobenzofuran derivative. However, they cannot be applied to the compound of the present invention because of an extremely low yield.

Considering the value of a 5-amino-2,3-dihydrobenzofuran compound, there is a demand for a process for producing the compound in a high yield under milder conditions which are suitable for industrial production.

Patent Document 1: WO 00/34262 A
Patent Document 2: JP 2003-104981 A
Patent Document 3: WO 98/08842 A non-Patent Document 1: Tetrahedron: Asymmetry, 10 (1999), 1521-1526,

DISCLOSURE OF THE INVENTION

Problem to be Solved by the Invention

In view of these circumstances, an object of the present invention is to provide an aromatic azo compound having a 2,3-dihydrobenzofuran ring bearing a diazo group at the 5-position of the ring, and a novel process for producing a 2,3-dihydrobenzofuran derivative bearing an amino or isoindolyl group at the 5-position of the ring by using the azo compound as a starting material, which is efficient, easy and simple and is suitable for industrial production.

Means for Solving the Problem

As a result of intensive studies to achieve the object, the present inventors have found that, when diazo coupling between a 2,3-dihydrobenzofuran derivative and a benzenediazonium salt having an electron-withdrawing group is carried out in a mixed solvent of water and a specific polar organic solvent, the reaction proceeds in a high yield. Thus, the present invention has been completed.

That is, the present invention provides:

(1) A process for producing an aromatic azo compound represented by the formula (III):

[Chemical formula 3]

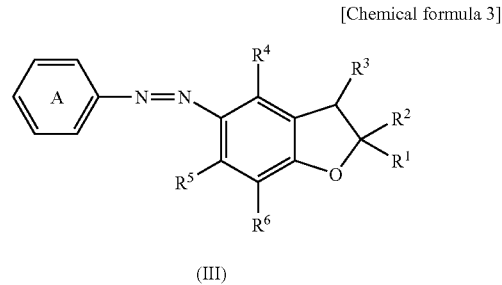

(III)

wherein the A ring is a benzene ring that has at least one electron-withdrawing group in addition to the diazonium group and may be further substituted; $R^1$ and $R^2$ are the same or different and are each independently $C_{1-6}$ alkyl; $R^3$ is optionally substituted aryl; and $R^4$, $R^5$ and $R^6$ are the same or different and are each independently hydrogen atom, $C_{1-6}$ alkyl, halogen, $C_{1-6}$ alkoxy or $C_{1-6}$ alkylthio, or a salt thereof, which comprises subjecting a benzenediazonium salt represented by the formula (I):

[Chemical formula 1]

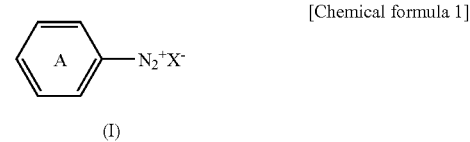

(I)

wherein the A ring is as defined above, and a compound represented by the formula (II):

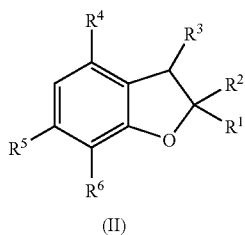

(II)

wherein $R^1$ to $R^6$ are as defined above; and $X^-$ is an anion, or a salt thereof, to diazo coupling in a mixed solvent substantially consisting of water and an organic solvent (other than carboxylic acid solvents), (2) The process according to the above (1), wherein a mixing ratio of water to the organic solvent is 1:99 to 99:1 in a volume ratio, (3) The process according to the above (2), wherein the organic solvent is acetonitrile, acetone or methyl acetate, (4) The process according to the above (1), wherein at least one of the electron-withdrawing groups substituted on the A ring is a nitro group, (5) The process according to the above (4), wherein the nitro group is substituted at the o- and/or p-positions of the A ring, (6) An aromatic azo compound represented by the formula (IIIa):

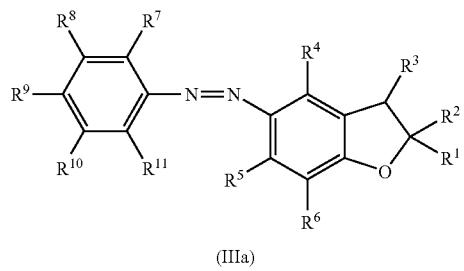

(IIIa)

wherein, $R^1$ and $R^2$ are the same or different and are each independently $C_{1-6}$ alkyl; $R^3$ is optionally substituted aryl; $R^4$, $R^5$ and $R^6$ are the same or different and are each independently hydrogen atom, $C_{1-6}$ alkyl, halogen, $C_{1-6}$ alkoxy or $C_{1-6}$ alkylthio; $R^7$, $R^8$, $R^{10}$ and $R^{11}$ are the same or different and are each independently hydrogen atom, optionally halogenated $C_{1-6}$ alkyl, nitro, $C_{1-6}$ alkoxysulfonyl, $C_{1-6}$ alkoxysulfinyl, N,N-di($C_{1-6}$ alkyl)aminosulfonyl, cyano, $C_{1-6}$ alkyl-carbonyl, $C_{1-6}$ alkoxy-carbonyl, N,N-di($C_{1-6}$ alkyl)carbamoyl or halogen atom; and $R^9$ is halogenated $C_{1-6}$ alkyl, nitro, $C_{1-6}$ alkoxysulfonyl, $C_{1-6}$ alkoxysulfinyl, N,N-di($C_{1-6}$ alkyl)aminosulfonyl, cyano, $C_{1-6}$ alkyl-carbonyl, $C_{1-6}$ alkoxy-carbonyl, N,N-di($C_{1-6}$ alkyl) carbamoyl or halogen atom, or a salt thereof, (7) A process for producing a compound represented by the formula (V):

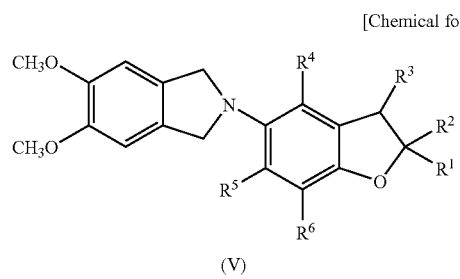

(V)

wherein $R^1$ to $R^6$ are as defined in the: above (1), which comprises subjecting the aromatic azo compound represented by the formula (III):

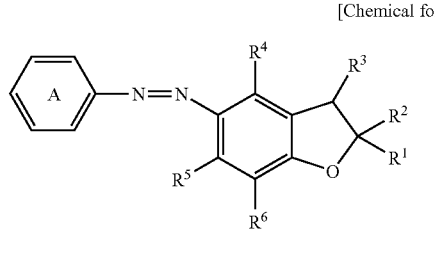

(III)

wherein the A ring and $R^1$ to $R^6$ are as defined in the above (1), or a salt thereof, obtained by the process according to the above (1) to a reducing reaction to obtain an amine compound represented by the formula (IV):

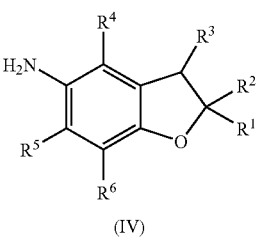

(IV)

wherein, $R^1$ to $R^6$ are as defined in the above (1), or a salt thereof; and reacting the amine compound (IV) with 1,2-bishalogenomethylveratrole.

Effects of the Invention

According to the process of the present invention, an aromatic azo compound having a 2,3-dihydrobenzofuran ring bearing a diazo group at the 5-position of the ring can be quantitatively prepared by conducting diazo coupling of a 2,3-dihydrobenzofuran derivative with a benzenediazonium salt having an electron-withdrawing group in a mixed solvent of water and a specific polar organic solvent. Therefore, by using the compound as a starting material, it is possible to provide a novel process for production of a 2,3-dihydrobenzofuran derivative having an isoindolyl group at the 5-position of the 2,3-dihydrobenzofuran ring useful for medical products, which is effective, easy and simple and is suitable for industrial production.

BEST MODE FOR CARRYING OUT THE INVENTION

Unless otherwise stated, the compounds herein may be racemates or optically active compounds.

In the above formulas (I) and (III), the A ring is a benzene ring that has at least one electron-withdrawing group in addition to the diazonium group and may be further substituted. Examples of the electron-withdrawing group substituted on the A ring include halogenated $C_{1-6}$ alkyl, nitro, $C_{1-6}$ alkoxysulfonyl, $C_{1-6}$ alkoxysulfinyl, N,N-di($C_{1-6}$ alkyl)aminosulfonyl, cyano, $C_{1-6}$ alkyl-carbonyl, $C_{1-6}$ alkoxy-carbonyl, N,N-di($C_{1-6}$ alkyl)carbamoyl, halogen atom, and the like.

Specific examples of the halogenated $C_{1-6}$ alkyl include trifluoromethyl, trifluoroethyl, and the like.

Specific examples of the $C_{1-6}$ alkoxysulfonyl include methoxysulfonyl, ethoxysulfonyl, and the like.

Specific examples of the $C_{1-6}$ alkoxysulfinyl include methoxysulfinyl, ethoxysulfinyl, and the like.

Specific examples of the N,N-di($C_{1-6}$ alkyl)aminosulfonyl include N,N-dimethylaminosulfonyl, N,N-diethylaminosulfonyl, and the like.

Specific examples of the $C_{1-6}$ alkyl-carbonyl include acetyl, propionyl, butyryl, isobutyryl, and the like.

Specific examples of the $C_{1-6}$ alkoxy-carbonyl include methoxycarbonyl, ethoxycarbonyl, propoxycarbonyl, tert-butoxycarbonyl, and the like.

Specific examples of the N,N-di($C_{1-6}$ alkyl)carbamoyl include N,N-dimethylcarbamoyl, N,N-diethylcarbamoyl, and the like.

Specific examples of the halogen atom include fluorine, chlorine, bromine, iodine, and the like.

Among them, nitro, $C_{1-6}$ alkoxysulfonyl, and the like are preferable electron-withdrawing groups. A position at which the electron-withdrawing group substituted is preferably the p- and o-positions of the A ring. The number of the electron-withdrawing group substituted on the A ring is preferably 1 to 3.

Examples of the substituent for "the benzene ring that may be further substituted" in "the benzene ring that has at least one electron-withdrawing group in addition to the diazonium group and may be further substituted" represented by the A ring include $C_{1-3}$ alkyl group, and the like.

Examples of the anion represented by $X^-$ in the benzenediazonium salt represented by the formula (I) include anions of halogens (e.g., fluoride, chloride, bromide and iodide ions) and tetrahalogenoborate (e.g., tetrafluoroborate), and the like.

In the formulas (II), (III), (IIIa), (IV) and (V), $R^1$ and $R^2$ are the same or different and are each independently $C_{1-6}$ alkyl; $R^3$ is optionally substituted aryl; $R^4$, $R^5$ and $R^6$ are the same or different and are each independently hydrogen atom, $C_{1-6}$ alkyl, halogen, $C_{1-6}$ alkoxy or $C_{1-6}$ alkylthio.

Examples of the $C_{1-6}$ alkyl represented by $R^1$ or $R^2$ include methyl, ethyl, propyl, isopropyl, butyl, isobutyl, sec-butyl, tert-butyl, pentyl, hexyl, and the like.

Examples of the "aryl group" in the "optionally substituted aryl" represented by $R^3$ include phenyl, naphthyl, and the like. Examples of the substituent of the "aryl group" in the "optionally substituted aryl" include (1) halogen atom (e.g., fluorine, chlorine, bromine, iodine, etc.); (2) $C_{1-3}$ alkylenedioxy (e.g., methylenedioxy, ethylenedioxy, etc.); (3) nitro; (4) cyano.; (5) optionally halogenated $C_{1-6}$ alkyl; (6) optionally halogenated $C_{2-6}$ alkenyl; (7) optionally halogenated $C_{2-6}$ alkynyl; (8) optionally halogenated $C_{3-6}$ cycloalkyl; (9) $C_{6-14}$ aryl (e.g., phenyl, 1-naphthyl, 2-naphthyl, biphenylyl, 2-anthryl, etc.); (10) optionally halogenated $C_{1-6}$ alkoxy; (11) optionally halogenated $C_{1-6}$ alkylthio or mercapto; (12) hydroxy; (13) amino; (14) mono($C_{1-6}$ alkyl)amino (e.g., methylamino, ethylamino, etc.); (15) mono($C_{6-14}$ aryl)amino (e.g., phenylamino, 1-naphthylamino, 2-naphthylamino, etc.); (16) di($C_{1-6}$ alkyl)amino (e.g., dimethylamino, diethylamino, etc.); (17) di($C_{6-14}$ aryl)amino (e.g., diphenylamino, etc.); (18) acyl; (19) acylamino; (20) acyloxy; (21) 5- to 7-membered saturated cyclic amino that may be substituted; (22) 5- to 10-membered aromatic heterocyclic group (e.g., 2- or 3-thienyl, 2-, 3- or 4-pyridyl, 2-, 3-, 4-, 5- or 8-quinolyl, 1-, 3-, 4- or 5-isoquinolyl, 1-, 2- or 3-indolyl, 2-benzothiazolyl, 2-benzo[b]thienyl, benzo[b]furanyl, etc.); (23) sulfo; (24) $C_{6-14}$ aryloxy (e.g., phenyloxy, naphthyloxy, etc.), and the like. Among them, preferred is $C_{1-6}$ alkyl.

The "aryl group" may have, for example, one to five, more preferably one to three substituents as described above at possible positions. When the aryl group has two or more substituents, those substituents may be the same or different.

Examples of the "optionally halogenated $C_{1-6}$ alkyl" include $C_{1-6}$ alkyl (e.g., methyl, ethyl, propyl, isopropyl, butyl, isobutyl, sec-butyl, tert-butyl, pentyl, hexyl, etc.) that may have, for example, one to five, preferably one to three halogen atoms (e.g., fluorine, chlorine, bromine, iodine, etc.). Specific examples include methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, and the like.

Examples of the "optionally halogenated $C_{2-6}$ alkenyl" include $C_{2-6}$ alkenyl (e.g., vinyl, allyl, isopropenyl, butenyl, isobutenyl, sec-butenyl, etc.) that may have, for example, one to five, preferably one to three halogen atoms (e.g., fluorine, chlorine, bromine, iodine, etc.). Specific examples include vinyl, allyl, isopropenyl, butenyl, isobutenyl, sec-butenyl, 3,3,3-trifluoro-1-propenyl, 4,4,4-trifluoro-1-butenyl, and the like.

Examples of the "optionally halogenated $C_{2-6}$ alkynyl" include $C_{2-6}$ alkynyl (e.g., ethynyl, propargyl, butynyl, 1-hexynyl, etc.) that may have, for example, one to five, preferably one to three halogen atoms (e.g., fluorine, chlorine, bromine, iodine, etc.). Specific examples include ethynyl, propargyl, butynyl, 1-hexynyl, 3,3,3-trifluoro-1-propynyl, 4,4,4-trifluoro-1-butynyl, and the like.

Examples of the "optionally halogenated $C_{3-6}$ cycloalkyl" include $C_{3-6}$ cycloalkyl (e.g., cyclopropyl, cyclobutyl, cyclopentyl, cyclohexyl, etc.) that may have, for example, one to five, preferably one to three halogen atoms (e.g., fluorine, chlorine, bromine, iodine, etc.). Specific examples include cyclopropyl, cyclobutyl, cyclopentyl, cyclohexyl, 4,4-dichlorocyclohexyl, 2,2,3,3-tetrafluorocyclopentyl, 4-chlorocyclohexyl, and the like.

Examples of the "optionally halogenated $C_{1-6}$ alkoxy" include $C_{1-6}$ alkoxy (e.g., methoxy, ethoxy, propoxy, isopropoxy, butoxy, isobutoxy, sec-butoxy, pentyloxy, hexyloxy, etc.) that may have, for example, one to five, preferably one to three halogen atoms (e.g., fluorine, chlorine, bromine, iodine, etc.). Specific examples include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, and the like.

Examples of the "optionally halogenated $C_{1-6}$ alkylthio" include $C_{1-6}$ alkylthio (e.g., methylthio, ethylthio, propylthio, isopropylthio, butylthio, sec-butylthio, tert-butylthio, etc.)

that may have, for example, one to five, preferably one to three halogen atoms (e.g., fluorine, chlorine, bromine, iodine, etc.). Specific examples include methylthio, difluoromethylthio, trifluoromethylthio, ethylthio, propylthio, isopropylthio, butylthio, 4,4,4-trifluorobutylthio, pentylthio, hexylthio, and the like.

Examples of the "acyl" include formyl, carboxy, carbamoyl, $C_{1-6}$ alkyl-carbonyl (e.g., acetyl, propionyl, etc.), $C_{3-6}$ cycloalkyl-carbonyl (e.g., cyclopropylcarbonyl, cyclopentylcarbonyl, cyclohexylcarbonyl, etc.), $C_{1-6}$ alkoxy-carbonyl (e.g., methoxycarbonyl, ethoxycarbonyl, propoxycarbonyl, tert-butoxycarbonyl, etc.), $C_{6-14}$ aryl-carbonyl (e.g., benzoyl, 1-naphthoyl, 2-naphthoyl, etc.), $C_{7-16}$ aralkyl-carbonyl (e.g., phenylacetyl, phenylpropionyl, etc.), $C_{6-14}$ aryloxy-carbonyl (e.g., phenoxycarbonyl, etc.), $C_{7-16}$ aralkyloxy-carbonyl (e.g., benzyloxycarbonyl, phenethyloxycarbonyl, etc.), 5- or 6-membered heterocyclic carbonyl (e.g., nicotinoyl, isonicotinoyl, 2-thenoyl, 3-thenoyl, 2-furoyl, 3-furoyl, morpholinocarbonyl, thiomorpholinocarbonyl, piperidinocarbonyl, 1-pyrrolidinylcarbonyl, etc.), mono($C_{1-6}$ alkyl)carbamoyl (e.g., methylcarbamoyl, ethylcarbamoyl, etc.), di($C_{1-6}$ alkyl)carbamoyl (e.g., dimethylcarbamoyl, diethylcarbamoyl, ethylmethylcarbamoyl, etc.), $C_{6-14}$ aryl-carbamoyl (e.g., phenylcarbamoyl, 1-naphthylcarbamoyl, 2-naphthylcarbamoyl, etc.), thiocarbamoyl, 5- or 6-membered heterocyclic carbamoyl (e.g., 2-pyridylcarbamoyl, 3-pyridylcarbamoyl, 4-pyridylcarbamoyl, 2-thienylcarbamoyl, 3-thienylcarbamoyl, etc.), $C_{1-6}$ alkylsulfonyl (e.g., methylsulfonyl, ethylsulfonyl, etc.), $C_{6-14}$ arylsulfonyl (e.g., phenylsulfonyl, 1-naphthylsulfonyl, 2-naphthylsulfonyl, etc.), $C_{1-6}$ alkylsulfinyl (e.g., methylsulfinyl, ethylsulfinyl, etc.), $C_{6-14}$ arylsulfinyl (e.g., phenylsulfinyl, 1-naphthylsulfinyl, 2-naphthylsulfinyl, etc.), and the like.

Examples of the "acylamino" include formylamino, $C_{1-6}$ alkyl-carbonylamino (e.g., acetylamino, etc.), $C_{6-14}$ aryl-carbonylamino (e.g., phenylcarbonylamino, naphthylcarbonylamino, etc.), $C_{1-6}$ alkoxy-carbonylamino (e.g., methoxycarbonylamino, ethoxycarbonylamino, propoxycarbonylamino, butoxycarbonylamino, etc.), $C_{1-6}$ alkylsulfonylamino (e.g., methylsulfonylamino, ethylsulfonylamino, etc.), $C_{6-14}$ arylsulfonylamino (e.g., phenylsulfonylamino, 2-naphthylsulfonylamino, 1-naphthylsulfonylamino, etc.), and the like.

Examples of the "acyloxy" include $C_{1-6}$ alkyl-carbonyloxy (e.g., acetoxy, propionyloxy, etc.), $C_{6-14}$ aryl-carbonyloxy (e.g., benzoyloxy, naphthylcarbonyloxy, etc.), $C_{1-6}$ alkoxy-carbonyloxy (e.g., methoxycarbonyloxy, ethoxycarbonyloxy, propoxycarbonyloxy, butoxycarbonyloxy, etc.), mono ($C_{1-6}$ alkyl)carbamoyloxy (e.g., methylcarbamoyloxy, ethylcarbamoyloxy, etc.), di ($C_{1-6}$ alkyl)carbamoyloxy (e.g., dimethylcarbamoyloxy, diethylcarbamoyloxy, etc.), $C_{6-14}$ arylcarbamoyloxy (e.g., phenylcarbamoyloxy, naphthylcarbamoyloxy, etc.), nicotinoyloxy, and the like.

Examples of the "5- to 7-membered saturated cyclic amino" in the "5- to 7-membered saturated cyclic amino that may be substituted" include morpholino, thiomorpholino, piperazine-1-yl, piperidino, pyrrolidine-1-yl, and the like. Examples of a "substituent" of the "5- to 7-membered saturated cyclic amino that may be substituted" include one to three substituents selected from $C_{1-6}$ alkyls (e.g., methyl, ethyl, propyl, isopropyl, butyl, isobutyl, sec-butyl, tert-butyl, pentyl, hexyl, etc.), $C_{6-14}$ aryls (e.g., phenyl, 1-naphthyl, 2-naphthyl, biphenylyl, 2-anthryl, etc.), 5- to 10-membered aromatic heterocyclic groups (e.g., 2- or 3-thienyl, 2-, 3- or 4-pyridyl, 2-, 3-, 4-, 5- or 8-quinolyl, 1-, 3-, 4- or 5-isoquinolyl, 1-, 2- or 3-indolyl, 2-benzothiazolyl, 2-benzo[b]thienyl, benzo[b]furanyl, etc.), and the like.

Examples of the $C_{1-6}$ alkyl represented by $R^4$, $R^5$ or $R^6$ include those described for the $C_{1-6}$ alkyl represented by $R^1$ or $R^2$.

Examples of the halogen represented by $R^4$, $R^5$ or $R^6$ include fluorine, chlorine, bromine and iodine.

Examples of the $C_{1-6}$ alkoxy represented by $R^4$, $R^5$ or $R^6$ include methoxy, ethoxy, propoxy, isopropoxy, butoxy, isobutoxy, sec-butoxy, pentyloxy, hexyloxy, and the like.

Examples of the $C_{1-6}$ alkylthio represented by $R^4$, $R^5$ or $R^6$ include methylthio, ethylthio, propylthio, isopropylthio, butylthio, sec-butylthio, tert-butylthio, and the like.

As $R^4$, $R^5$ or $R^6$, $C_{1-6}$ alkyl is preferred.

In the formula (IIIa), $R^7$, $R^8$, $R^{10}$ and $R^{11}$ are the same or different and are each independently hydrogen atom, optionally halogenated $C_{1-6}$ alkyl, nitro, $C_{1-6}$ alkoxysulfonyl (e.g., methoxysulfonyl, ethoxysulfonyl, etc.), $C_{1-6}$ alkoxysulfinyl (e.g., methoxysulfinyl, ethoxysulfinyl, etc.), N,N-di($C_{1-6}$ alkyl)aminosulfonyl (e.g., N,N-dimethylaminosulfonyl, etc.), cyano, $C_{1-6}$ alkyl-carbonyl (e.g., acetyl, propionyl, etc.), $C_{1-6}$ alkoxy-carbonyl (e.g., methoxycarbonyl, ethoxycarbonyl, etc.), N,N-di($C_{1-6}$ alkyl)carbamoyl (e.g., N,N-dimethylcarbamoyl, N,N-diethylcarbamoyl, etc.) or halogen atom (e.g., fluorine, chlorine, bromine, iodine).

Examples of the "optionally halogenated $C_{1-6}$ alkyl" represented by $R^7$, $R^8$, $R^{10}$ or $R^{11}$ include $C_{1-6}$ alkyl (e.g., methyl, ethyl, propyl, isopropyl, butyl, isobutyl, sec-butyl, tert-butyl, pentyl, hexyl, etc.) that may have, for example, one to five, preferably one to three halogen atoms (e.g., fluorine, chlorine, bromine, iodine). Specific examples include methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, and the like.

When the compound (IIIa) contains a basic group such as an amino group, examples of a salt thereof to be used include inorganic salts (e.g., hydrochloride, phosphate, hydrobromide, sulfate, etc.) and organic salts (e.g., acetate, trifluoroacetate, formate, propionate, fumarate, maleate, succinate, tartrate, citrate, malate, oxalate, benzoate, methanesulfonate, benzenesulfonate, etc.), and the like. When the compound contains an acidic group such as a carboxy group, the compound may form a salt with inorganic bases (e.g., alkaline or alkaline earth metals such as sodium, potassium, calcium, magnesium, etc.), organic bases (e.g., tri($C_{1-6}$ alkyl)amines such as triethylamine), or ammonia.

In the formula (IIIa), $R^9$ is halogenated $C_{1-6}$ alkyl (e.g., trichloromethyl, trifluoromethyl, etc.), nitro, $C_{1-6}$ alkoxysulfonyl (e.g., methoxysulfonyl, ethoxysulfonyl, etc.), $C_{1-6}$ alkoxysulfinyl (e.g., methoxysulfinyl, ethoxysulfinyl, etc.), N,N-di($C_{1-6}$ alkyl)aminosulfonyl (e.g., N,N-dimethylaminosulfonyl, etc.), cyano, $C_{1-6}$ alkyl-carbonyl (e.g., acetyl, propionyl, etc.), $C_{1-6}$ alkoxy-carbonyl (e.g., methoxycarbonyl, ethoxycarbonyl, etc.), N,N-di($C_{1-6}$ alkyl)-carbamoyl (e.g., N,N-dimethylcarbamoyl, N,N-diethylcarbamoyl, etc.) or halogen atom (e.g., fluorine, chlorine, bromine, iodine).

The benzenediazonium salt represented by the formula (I) can be prepared by a per se known method such as a method described in, for example, "SHIN-JIKKENKAGAKU-KOUZA (New Series of Experimental Chemistry)", vol 14, p.

1564-p. 1573, or a modification thereof. For example, the salt can be prepared by dissolving an aniline derivative represented by the formula (I'):

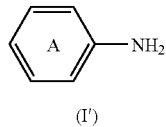

[Chemical formula 8]

(I')

wherein the A ring is as defined in the formula (I), dissolved in hydrochloric acid and adding an aqueous sodium nitrite solution to the resulting solution with ice-cooling. The resultant benzenediazonium salt can be isolated from the reaction mixture and used in the next diazo coupling step, or can be used in the diazo coupling reaction in situ without isolation by adding a polar organic solvent and a 2,3-dihydrobenzofuran derivative in a specific ratio to a reaction mixture.

The azo coupling of the 2,3-dihydrobenzofuran derivative represented by the formula (II) with the benzenediazonium salt represented by the formula (I) in the present invention proceeds in a high yield by carrying out the reaction in a mixed solvent substantially consisting of water and an organic solvent. Any organic solvent inert to the reaction can be used, and examples thereof include nitrites (e.g., acetonitrile, propionitrile, etc.), esters (e.g., methyl acetate, ethyl acetate, ethyl propionate, etc.), ketones (e.g., acetone, 2-butanone, etc.), alcohols (e.g., methanol, ethanol, propanol, methoxyethanol, etc.), ethers (e.g., ethyl ether, tetrahydrofuran, dioxane, 1,2-dimethoxyethane, etc.), and the like. The organic solvent can be used alone or in combination of two or more kinds thereof. As used herein, the term "substantially consisting of" means that, the mixed solvent includes, in addition to a mixed solvent which does not contain other solvents, i.e., a solvent other than water and an organic solvent (excluding carboxylic acid solvents), a mixed solvent which contains other solvent(s) in such an amount that does not interfere with the reaction to an unpractical degree. As used herein, the carboxylic acid solvent refers a solvent having a carboxyl group. "The amount that does not interfere with the reaction to an unpractical degree" can be varied according to a particular kind of the other solvent, and is generally not less than 70% (v/v), preferably not less than 80% (v/v), and more preferably not less than 90% (v/v) of the mixed solvent. Examples of the other solvent include, but not limited thereto, carboxylic acids (e.g., carboxylic acid solvent such as formic acid, acetic acid, propionic acid and butyric acid), amides (e.g., dimethylformamide, dimethylacetamide, N-methylpyrrolidone, hexamethylphosphoramide, etc.), dimethylsulfoxide, and the like.

Specifically, preferred organic solvents are acetonitrile, acetone and methyl acetate. A mixed ratio of water to organic solvent is 1:99 to 99:1, preferably 10:90 to 90:10 in a volume ratio.

In the azo coupling, 0.1 to 10 mol of benzenediazonium salt represented by the formula (I) is used per one mol of the 2,3-dihydrobenzofuran derivative represented by the formula (II). The reaction temperature is −20 to 200° C., and preferably 0 to 150° C. The reaction time is 0.5 to 100 hours. If necessary, the resultant compound of the formula (III) can be easily isolated by a conventional method such as extraction and crystallization.

The compound represented by the formula (V) can be prepared according to the following scheme.

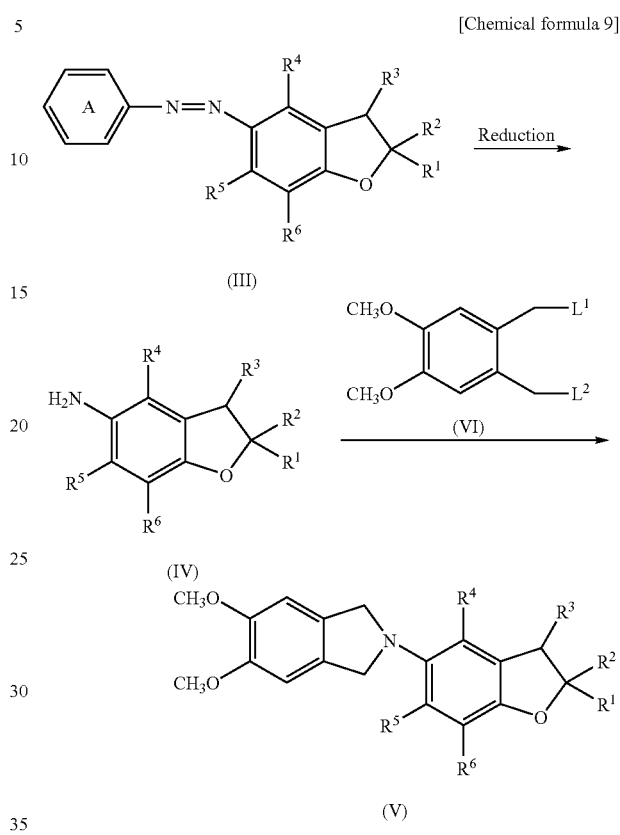

wherein $L^1$ and $L^2$ are leaving groups; the others are as defined as above.

(1) Reducing Reaction of Compound (III) to Compound (IV)

The reduction can be carried out by sodium dithionite as a reducing agent or catalytic reduction with a catalyst such as palladium, Raney nickel, or the like. Among them, sodium dithionite is preferred. When using sodium dithionite as a reducing agent, an amount of sodium dithionite used is 0.5 to 20 equivalents relative to the compound (III). The reaction temperature is −20 to 200° C., and preferably 0 to 150° C. The reducing reaction proceeds in a high yield by carrying out the reaction in a mixed solvent of water and an organic solvent. Any organic solvent inert to the reaction can be used, and examples thereof include nitriles (e.g., acetonitrile, propionitrile, etc.), esters (e.g., methyl acetate, ethyl acetate, ethyl propionate, etc.), ketones (e.g., acetone, 2-butanone, etc.), carboxylic acids (e.g., formic acid, acetic acid, propionic acid, butyric acid, etc.), alcohols (e.g., methanol, ethanol, propanol, and methoxyethanol), ethers (e.g., ethyl ether, tetrahydrofuran, dioxane, 1,2-dimethoxyethane, etc.), amides (e.g., dimethylformamide, dimethylacetamide, N-methylpyrrolidone, hexamethylphosphoramide, etc.), dimethylsulfoxide, and the like, as well as a mixture thereof. When employing catalytic reduction for this reduction, the reaction temperature is −20 to 200° C., and preferably 0 to 150° C. The reducing reaction can be carried out in any solvent inert to the reaction, and examples thereof include nitriles (e.g., acetonitrile, propionitrile, etc.), esters (e.g., methyl acetate, ethyl acetate, ethyl propionate, etc.), ketones (e.g., acetone, 2-butanone, etc.), carboxylic acids (e.g., formic acid, acetic acid, propionic acid, butyric acid, etc.), alcohols (e.g., methanol, ethanol, propanol, methoxyethanol, etc.), ethers (e.g., ethyl ether, tetrahydrofuran, dioxane, 1,2-dimethoxyethane, etc.), amides (e.g., dimethylformamide, dimethylacetamide, N-methylpyrrolidone, hexamethylphosphoramide, etc.), dimethylsulfoxide, water, and the like, as well as a mixture thereof, and the like.

(2) Reaction from Compound (IV) to Compound (V)

The compound (V) can be prepared by reacting the compound (IV) with the compound (VI), if desired, in the presence of a base.

Examples of the leaving groups represented by $L^1$ and $L^2$ in the compound (VI) include hydroxy, halogen atom (e.g., fluorine, chlorine, bromine, iodine, etc.), optionally halogenated $C_{1-5}$ alkylsulfonyloxy (e.g., methanesulfonyloxy, ethanesulfonyloxy, trichloromethanesulfonyloxy, etc.), optionally substituted $C_{6-10}$ arylsulfonyloxy, and the like. Examples of the "optionally substituted $C_{6-10}$ arylsulfonyloxy" include $C_{6-10}$ arylsulfonyloxy that may have one to three substituents selected from $C_{1-6}$ alkyl (e.g., methyl, ethyl, propyl, isopropyl, butyl, isobutyl, sec-butyl, tert-butyl, pentyl, hexyl, etc.), $C_{1-6}$ alkoxy (e.g., methoxy, ethoxy, propoxy, isopropoxy, butoxy, isobutoxy, sec-butoxy, pentyloxy, hexyloxy, etc.) and nitro (e.g., phenylsulfonyloxy, naphthylsulfonyloxy, etc.). Specific examples include benzenesulfonyloxy, m-nitrobenzenesulfonyloxy, p-toluenesulfonyloxy, and the like.

The amount of the compound (VI) to be used is about 1.0 to about 5.0 mol, and preferably about 1.0 to about 2.0 mol per one mol of the compound (IV).

Examples of the "base" include basic salts such as sodium carbonate, potassium carbonate, cesium carbonate, sodium hydrogen carbonate, etc.; aromatic amines such as pyridine, lutidine, etc.; tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc.; alkali metal hydrides such as sodium hydride, potassium hydride, etc.; metal amides such as sodium amide, lithium diisopropylamide, lithium hexamethyldisilazide, etc.; metal alkoxides such as sodium methoxide, sodium ethoxide, potassium tert-butoxide, etc.; and the like.

The amount of the base to be used is about 1.0 to about 10.0 mol, and preferably about 2.0 to about 5.0 mol per one mol of the compound (IV). If desired, the compound (V) can also be prepared in the presence of a quaternary ammonium salt together with the base.

Examples of the "quaternary ammonium salt" include tetrabutylammonium iodide, and the like.

The amount of the quaternary ammonium salt to be used is about 0.1 to about 2.0 mol, and preferably about 0.5 to about 1.0 mol per one mol of the compound (IV).

It is advantageous to carry out the reaction in a solvent inert to the reaction. Such a solvent is not specifically limited as long as the reaction proceeds, and examples of the solvent preferably include alcohols such as methanol, ethanol, propanol, etc.; ethers such as diethyl ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; halogenated hydrocarbons such as dichloromethane, chloroform, carbon tetrachloride, 1,2-dichloroethane, etc.; nitrites such as acetonitrile, propionitrile. etc.; sulfoxides such as dimethyl sulfoxide, etc.; and the like, as well as a mixed solvent thereof, and the like.

The reaction time is usually about 30 minutes to about 48 hours, preferably about 1 to about 24 hours. The reaction temperature is usually about −20 to about 200° C., preferably about 0 to about 150° C.

The optically active compound (V) can be prepared by using the optically active compound (IV) as a starting material. The compound (IV) can be optically resolved by a known method. Specifically, the optically active compound (IV) or a salt thereof can be prepared by inducing the compound (IV) or a salt thereof into a salt with an optically active acidic compound and optically resolving it, as described below.

First, in an appropriate solvent, the compound (IV) is reacted with an optically active acidic compound as an acidic resolving agent to form a diastereomer salt. Examples of the optically active acidic compound include an optically active tartaric acid derivative such as optically active O,O'-di-acyltartaric acid derivative; an optically active amino acid derivative such as optically active N-acylamino acid; an optically active phosphoric acid derivative represented by the formula:

[Chemical formula 10]

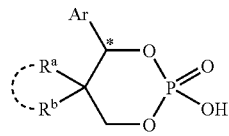

wherein Ar is an aromatic hydrocarbon group that may be substituted; $R^a$ and $R^b$ are each independently hydrogen atom, optionally substituted lower alkyl group, optionally substituted lower alkoxy group, halogen atom or nitro group, or $R^a$ and $R^b$ bind together to form an alkylene or alkylenedioxy group that may be substituted; and an asterisk indicates a position of an asymmetric carbon, and the like.

The preferred acyl group of the O,O'-di-acyltartaric acid derivative is, for example, a lower ($C_{1-6}$) alkanoyl group such as acetyl, propionyl, butyryl, valeryl, etc.; and an aroyl group such as benzoyl, p-chlorobenzoyl, naphthoyl, etc. Most preferred O,O'-di-acyltartaric acid is O,O'-di-(p-toluoyl)tartaric acid.

The preferred N-acyl group of the N-acylamino acid derivative is, for example, a lower ($C_{1-6}$) alkanoyl group such as acetyl, propionyl, butyryl, valeryl, etc.; and an aroyl group such as benzoyl, p-chlorobenzoyl, naphthoyl, etc. Examples of the amino acid include α-phenylglycine. Most preferred N-acylamino acid derivative is N-(3,5-dinitrobenzoyl)-α-phenylglycine.

The optically active phosphoric acid derivative can be easily obtained according to methods, for example, those described in JP 61-103886 A, J. Org. Chem., 50, 4508 (1985), etc., and some compounds are commercially available easily. Specific examples include 2-hydroxy-5,5-dimethyl-4-phenyl-1,3,2-dioxaphospholinane 2-oxide, 4-(2-chlorophenyl)-2-hydroxy-5,5-dimethyl-1,3,2-dioxaphospholinane 2-oxide, 4-(2,4-dichlorophenyl)-2-hydroxy-5,5-dimethyl-1,3,2-dioxaphospholinane 2-oxide, 2-hydroxy-4-(2-methoxyphenyl)-5,5-dimethyl-1,3,2-dioxaphospholinane 2-oxide, 2-hydroxy-5,5-dimethyl-4-(1-naphthyl)-1,3,2-dioxaphospholinane 2-oxide, and the like.

The resultant compound (V) has low toxicity, and has excellent medical effects such as a neurotrophic factor-like effect, a neurotrophic factor activity-enhancing effect, a neurodegeneration inhibiting effect, a β-amyloid cytotoxicity-suppressing effect, a nerve regeneration/neogenesis facilitating effect and a growth/differentiation facilitating effect in neural stem cells and/or nerve cells, and thus is useful as a pharmaceutical for mammalian animals including human. The compounds (III) and (IIIa) are useful as intermediates for preparing the compound (V). More specifically, the compound (V) is effective for nerve degenerative diseases (e.g., Alzheimer's disease, Parkinson's disease, amyotrophic lateral sclerosis (ALS), Huntington's disease and spinocerebellar degeneration), psychoneurotic diseases (e.g., schizophrenia), head injury, spinal cord injury, cerebrovascular accident, cerebrovascular dementia, peripheral neuropathies (e.g., diabetic neuropathy), and the like, and thus is employed as a prophylactic/therapeutic drug for these diseases. The compound (V) is also useful as a prophylactic/therapeutic drug for vascular diseases such as cerebral apoplexy, inflammations, and the like.

Preferred examples of the compound (V) include 5,6-dimethoxy-2-[2,2,4,6,7-pentamethyl-3-(4-methylphenyl)-2,3-dihydro-1-benzofuran-5-yl]isoindoline, 5,6-dimethoxy-2-[3-(4-isopropylphenyl)-2,2,4,6,7-pentamethyl-2,3-dihydro-1-benzofuran-5-yl]isoindoline, (R)-5,6-dimethoxy-2-[2,2,4,6,7-pentamethyl-3-(4-methylphenyl)-2,3-dihydro-1-benzofuran-5-yl]isoindoline or (R)-5,6-dimethoxy-2-[2,2,4,6,7-pentamethyl-3-(4-methylphenyl)-2,3-dihydro-1-benzofuran-5-yl]isoindoline hydrochloride, and the like.

The compound (V) can be used as a prophylactic/therapeutic drug for diseases described above by formulating the compound (V) into a pharmaceutical composition and/or preparation according to known methods, for example, described in EP483772A, WO 00/34262 and WO 03/051355.

The present invention is further illustrate in detail by the following Examples, Reference Example and Comparative Example, but does not intend to be limited by these Examples, and may be varied without departing from the scope of the present invention.

NMR (nuclear magnetic resonance) spectra were measured with a Bruker DPX300 spectrometer (1H-NMR: 300 MHz). The internal reference was tetramethylsilane, and all of $\delta$ values were shown by ppm. Abbreviations used herein were as follows.

CDCl$_3$: deuterated chloroform, m: multiplet, s: singlet, brs: broad singlet.

EXAMPLE 1

1-(4-Nitrophenyl)-2-[2,2,4,6,7-pentamethyl-3-(4-methylphenyl)-2,3-dihydro-1-benzofuran-5-yl]diazene 4-Nitroaniline (10.4 g) was dissolved in 2N hydrochloric acid (150 mL) by heating, and then cooled to 0 to 5° C. To the solution was added a solution of sodium nitrite (5.2 g) in water (15 mL), and the mixture was stirred for 15 minutes. To the mixture were added 2,2,4,6,7-pentamethyl-3-(4-methylphenyl)-2,3-dihydro-1-benzofuran (14.0 g) and acetonitrile (150 mL). The reaction mixture was stirred at 65 to 70° C. for one hour under a nitrogen atmosphere, and then allowed to cool to room temperature. Precipitated crystals were collected by filtration, and washed with 1N hydrochloric acid and water. The crystals were dried under reduced pressure to obtain the title compound as a brown solid (21.0 g, yield 100%).

$^1$H-NMR(CDCl$_3$) $\delta$: 1.07(3H,s), 1.54(3H,s), 2.08(3H,s), 2.26(3H,s), 2.31(3H,s), 2.53(3H,s), 4.19(1H,s), 6.50-7.10 (4H,m), 7.84-7.89(2H,m), 8.30-8.35(2H,m)

EXAMPLE 2

[2,2,4,6,7-Pentamethyl-3-(4-methylphenyl)-2,3-dihydro-1-benzofuran-5-yl]amine

The above-obtained 1-(4-nitrophenyl)-2-[2,2,4,6,7-pentamethyl-3-(4-methylphenyl)-2,3-dihydro-1-benzofuran-5-yl]diazene (6.0 g) and sodium dithionite (14.6 g) were added to a mixture of methanol (30 mL) and water (30 mL), and the mixture was stirred at 65 to 70° C. for 2 hours under a nitrogen atmosphere. The mixture was cooled to room temperature, and further stirred at 0 to 5° C. for one hour. Precipitated crystals were collected by filtration, and washed with a mixture of methanol and water again to obtained wetted crystals. The wetted crystals were added to a mixture of toluene and 2N aqueous sodium hydroxide. An organic layer was separated and concentrated. The concentrate was recrystallized from a mixture of water and methanol, and the resultant crystals were dried under reduced pressure to obtain the title compound (3.5 g., yield 86%).

$^1$H-NMR(CDCl$_3$) $\delta$: 0.99(3H,s), 1.47(3H,s), 1.77(3H,s), 2.12(3H,s), 2.19(3H,s), 2.30(3H,s), 3.23(2H,brs), 4.08(1H, s), 6.50-7.10(4H,m)

EXAMPLE 3

[2,2,4,6,7-Pentamethyl-3-(4-methylphenyl)-2,3-dihydro-1-benzofuran-5-yl]amine

4-Nitroaniline (1.9 g) was dissolved in 2N hydrochloric acid (36 mL) at 60° C., and then cooled to 0 to 5° C. To the resultant solution was added a solution of sodium nitrite (0.96 g) in water (3 mL), and the mixture was stirred for 15 minutes. To the mixture were added 2,2,4,6,7-pentamethyl-3-(4-methylphenyl)-2,3-dihydro-1-benzofuran (2.6 g) and acetonitrile (36 mL). The resultant mixture was stirred at 65 to 70° C. for 2 hours under a nitrogen atmosphere. The mixture was cooled to room temperature, stirred for one hour, and then further stirred at 0 to 5° C. for one hour. Precipitated crystals were collected by filtration, and washed twice with water. (36 mL) to obtain wetted crystals.

The resultant wetted crystals and sodium dithionite (9.7 g) were added to a mixture of methanol (30 mL) and water (10 mL), and stirred at 65 to 70° C. for 2 hours under a nitrogen atmosphere. To the mixture was added water (20 mL) and stirred for one hour, and then allowed to cool to room temperature, and further stirred at 0 to 5° C. for one hour. Precipitated crystals were collected by filtration, and washed with a mixture of methanol (10 mL) and water (10 mL) to obtain wetted crystals. The wetted crystals were added to a mixture of toluene (20 mL) and 2N aqueous sodium hydroxide (20 mL), and dissolved by heating at 60° C. An organic layer was separated and concentrated. The concentrate was dissolved in methanol (10 mL) by heating, and to the resultant solution was added water (10 mL). The mixture was stirred at 65 to 70° C. for one hour, and then allowed to cool to room temperature, and further stirred at 0 to 5° C. for one hour. Precipitated crystals were collected by filtration, and washed with a mixture of methanol (5 mL) and water (5 mL). The crystals were dried under reduced pressure to obtain the title compound (2.4 g, yield 87%).

EXAMPLE 4

[2,2,4,6,7-Pentamethyl-3-(4-methylphenyl)-2,3-dihydro-1-benzofuran-5-yl]amine

4-Nitroaniline (0.16 g) was dissolved in 2N hydrochloric acid (3 mL) at 60° C., and then cooled to 0 to 5° C. To the resultant solution was added sodium nitrite (79 mg), and stirred for 15 minutes. To the mixture were added 2,2,4,6,7-pentamethyl-3-(4-methylphenyl)-2,3-dihydro-1-benzofuran (0.27 g) and a solvent (3 mL), and stirred under a nitrogen atmosphere. After completion of the reaction, a sample was taken from the mixture and its composition was measured with HPLC (*1). Solvents, reaction conditions and results of measurement are shown in Table 1.

TABLE 1

| Solvent | Reaction conditions | Area percent of starting material (%) | Area percent of title compound (%) |
|---|---|---|---|
| Acetic acid (Comparative Example) | 65-70° C., 3 h | Not detected | 7.9 |
| Acetone | 65-70° C., 3 h | 36.0 | 20.7 |
| Methyl acetate (*2) | 45-50° C., 3 h | 32.3 | 41.8 |
| Acetonitrile (*3) | 65-70° C., 3 h | 0.8 | 98.1 |

(*1): In measurement, a column was YMC-pack AS-302, a mobile phase was 0.02 M potassium dihydrogen phosphate/acetonitrile (2/8), a temperature was 25° C., a measurement wavelength was 230 nm, a flow rate was 1 mL/min.
(*2): 1.2 equivalents of sodium nitrite was used relative to the starting material.
(*3): 0.30 g of the starting material, and proportional amounts of other reagents and solvents were used.

REFERENCE EXAMPLE 1

2,2,4,6,7-Pentamethyl-3-(4-methylphenyl)-2,3-dihydro-1-benzofuran

A mixture of 4-bromotoluene (1.71 g), isobutylaldehyde (1.44 g), palladium acetate (0.11 g), 10% solution of tri-t-butylphosphine in hexane (2.0 g), cesium carbonate (3.91 g) and N,N-dimethylformaldehyde (17 mL) was stirred at 110° C. for one hour under a nitrogen atmosphere, and then cooled to room temperature. To the mixture was added 2N hydrochloric acid, and the resultant mixture was extracted with toluene. The organic layer was washed with water, and concentrated. To the concentrate were added toluene (10 mL), 2,3,5-trimethylphenol (1.09 g) and trifluoromethanesulfonic acid (71 μL), and stirred for 2 hours with heat refluxing, and then cooled to room temperature. The organic layer was separated, washed with a saturated sodium hydrogen carbonate aqueous solution and water, and then concentrated. The concentrate was recrystallized from a mixture of water and isopropanol to obtain 1.35 g of title compound.

$^1$H-NMR(CDCl$_3$)δ: 1.10(3H,s), 1.49(3H,s), 1.83(3H,s), 2.14(3H,s), 2.23(3H,s), 3.00(3H,s), 4.09(1H,s), 6.47(1H,s), 6.47-7.05(4H,m)

COMPARATIVE EXAMPLE 1

4-Nitroaniline (304 mg) was dissolved in 2N hydrochloric acid (6 mL) by heating, and then cooled to 0 to 5° C. To the resultant solution was added a solution of sodium nitrite (152 mg) in water (1 mL), and the mixture was stirred for 15 hours. To the mixture were added 2,2,4,6,7-pentamethyl-3-(4-methylphenyl)-2,3-dihydro-1-benzofuran (560 mg) and acetic acid (6 mL). The mixture was stirred at room temperature for 3 hours, but the reaction did not proceed, and the starting materials were recovered.

INDUSTRIAL APPLICABILITY

As described above, according to the present invention, it is possible to provide an aromatic azo compound having a 2,3-dihydrobenzofuran ring bearing a diazo group at the 5-position of the ring, and a novel process for producing a 2,3-dihydrobenzofuran derivative bearing an amino or isoindolyl group at the 5-position of the ring by using the azo compound as a starting material, which is efficient, easy and simple and is suitable for industrial production.

The invention claimed is:
1. A process for producing an aromatic azo compound represented by the formula (III):

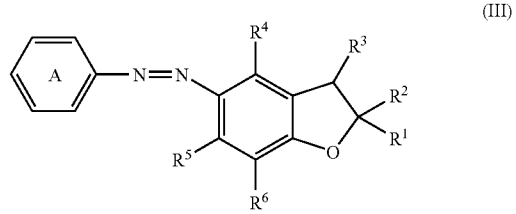

wherein the A ring is a benzene ring that has at least one electron-withdrawing group in addition to the diazonium group and may be further substituted; $R^1$ and $R^2$ are the same or different and are each independently $C_{1-6}$ alkyl; $R^3$ is optionally substituted aryl; and $R^4$, $R^5$ and $R^6$ are the same or different and are each independently hydrogen atom, $C_{1-6}$ alkyl, halogen, $C_{1-6}$ alkoxy or $C_{1-6}$ alkylthio, or a salt thereof, which comprises subjecting a benzenediazonium salt represented by the formula (I):

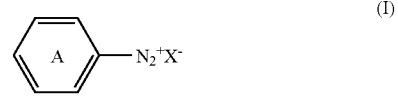

wherein the A ring is as defined above, and a compound represented by the formula (II):

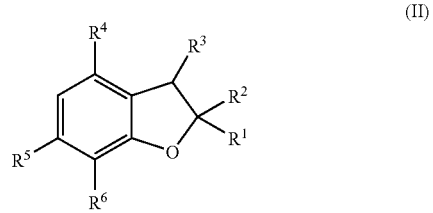

wherein $R^1$ to $R^6$ are as defined above; and $X^-$ is an anion, or a salt thereof, to diazo coupling in a mixed solvent substantially consisting of water and an organic solvent (other than carboxylic acid solvents).

2. The process according to claim 1, wherein a mixing ratio of water to the organic solvent is 1:99 to 99:1 in a volume ratio.

3. The process according to claim 2, wherein the organic solvent is acetonitrile, acetone or methyl acetate.

4. The process according to claim 1, wherein at least one of the electron-withdrawing groups substituted on the A ring is a nitro group.

5. The process according to claim 4, wherein the nitro group is substituted at the o- and/or p-positions of the A ring.

6. An aromatic azo compound represented by the formula (IIIa):

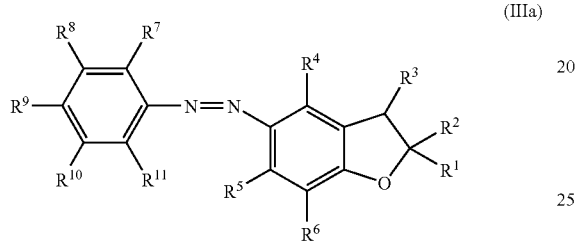

wherein, $R^1$ and $R^2$ are the same or different and are each independently $C_{1-6}$ alkyl; $R^3$ is optionally substituted aryl; $R^4$, $R^5$ and $R^6$ are the same or different and are each independently hydrogen atom, $C_{1-6}$ alkyl, halogen, $C_{1-6}$ alkoxy or $C_{1-6}$ alkylthio; $R^7$, $R^8$, $R^{10}$ and $R^{11}$ are the same or different and are each independently hydrogen atom, optionally halogenated $C_{1-6}$ alkyl, nitro, $C_{1-6}$ alkoxysulfonyl, $C_{1-6}$ alkoxysulfinyl, N,N-di($C_{1-6}$ alkyl)aminosulfonyl, cyano, $C_{1-6}$ alkyl-carbonyl, $C_{1-6}$ alkoxy-carbonyl, N,N-di($C_{1-6}$ alkyl)carbamoyl or halogen atom; and $R^9$ is halogenated $C_{1-6}$ alkyl, nitro, $C_{1-6}$ alkoxysulfonyl, $C_{1-6}$ alkoxysulfinyl, N,N-di($C_{1-6}$ alkyl)aminosulfonyl, cyano, $C_{1-6}$ alkyl-carbonyl, $C_{1-6}$ alkoxy-carbonyl, N,N-di($C_{1-6}$ alkyl)carbamoyl or halogen atom, or a salt thereof.

7. A process for producing a compound represented by the formula (V):

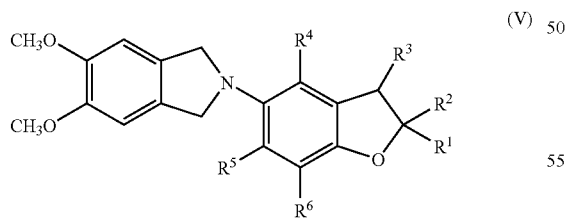

wherein $R^1$ and $R^2$ are the same or different and are each independently $C_{1-6}$ alkyl; $R^3$ is optionally substituted aryl; and $R^4$, $R^5$ and $R^6$ are the same or different and are each independently hydrogen atom, $C_{1-6}$ alkyl, halogen, $C_{1-6}$ alkoxy or $C_{1-6}$ alkylthio, which comprises:

(i) subjecting an aromatic azo compound represented by the formula (III):

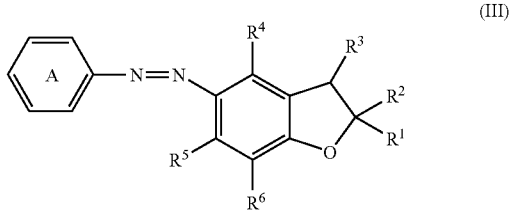

wherein the A ring is a benzene ring that has at least one electron-withdrawing group in addition to the diazonium group and may be further substituted, and $R^1$ to $R^6$ are as defined above, or a salt thereof, to a reducing reaction to obtain an amine compound represented by the formula (IV):

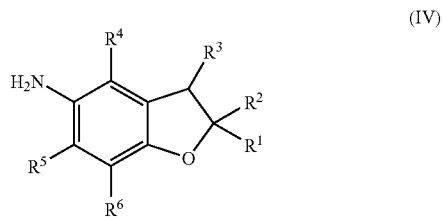

wherein, $R^1$ to $R^6$ are as defined above, or a salt thereof; and (ii) reacting the amine compound (IV) with 1,2-bishalogenomethylveratrole;

wherein the aromatic azo compound represented by the formula (III) is obtained by a process comprising subjecting a benzenediazonium salt represented by the formula (I):

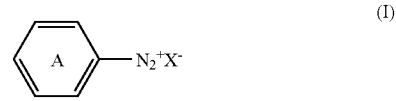

wherein the A ring is as defined above, and a compound represented by the formula (II):

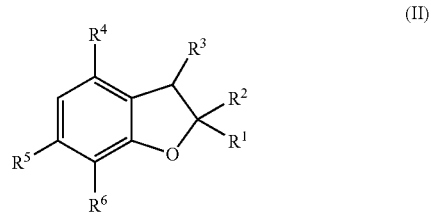

wherein $R^1$ to $R^6$ are as defined above and $X^-$ is an anion, or a salt thereof, to diazo coupling in a mixed solvent substantially consisting of water and an organic solvent other than carboxylic acid solvents.

* * * * *